US00PP34264P2

(12) United States Plant Patent
Sheehan

(10) Patent No.: US PP34,264 P2
(45) Date of Patent: May 24, 2022

(54) GRAPEVINE PLANT NAMED 'SHEEGENE 105'

(50) Latin Name: *Vitis vinifera*
Varietal Denomination: Sheegene 105

(71) Applicant: SNFL Australia Pty Ltd., Mildura (AU)

(72) Inventor: Timothy P. Sheehan, Vancouver, WA (US)

(73) Assignee: SNFL Australia Pty Ltd., Mildura (AU)

( * ) Notice: Subject to any disclaimer, the term of this patent is extended or adjusted under 35 U.S.C. 154(b) by 0 days.

(21) Appl. No.: 17/184,190

(22) Filed: Feb. 24, 2021

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206
See application file for complete search history.

(56) References Cited

PUBLICATIONS

Wood, Marcia, "'Autumn Royal' Grape Is a Luscious Aristocrat," USDA—Agricultural Research Service, *Research News*, Oct. 23, 1997. Accessible at < https://www.ars.usda.gov/news-events/news/research-news/1997/autumn-royal-grape-is-a-luscious-aristocrat/>.
CPVO Variety Data Sheet for "Summer Royal", published on Apr. 15, 2004.

*Primary Examiner* — Susan McCormick Ewoldt
(74) *Attorney, Agent, or Firm* — Dentons US LLP

(57) ABSTRACT

'Sheegene 105' is a new and distinct grapevine plant with novel characteristics that include naturally loose bunches. The berries produced by 'Sheegene 105' are black and seedless with a very crisp texture and no detectable seed traces. The berries produced by 'Sheegene 105' are medium, weighing 6-7 g/berry on average, and are harvested in mid July in Spain (Murcia Region).

1 Drawing Sheet

Latin name of the genus and species of the plant claimed: *Vitis vinifera.*

Cultivar denomination: 'Sheegene 105'.

BACKGROUND OF THE INVENTION

The present invention relates to a new distinct variety of seedless grapevine named 'Sheegene 105'. The variety originated from a hybridization performed in Mildura, Victoria, Australia during 2004 between 'Stanley Seedless' (unpatented), as the pollen parent, and 'Autumn Royal' (unpatented), as the seed parent. Abortive seed traces were embryo cultured and the resulting plant was planted in an evaluation block during 2006. The first evaluation of fruit produced by "Sheegene 105" was performed during 2009. 'Sheegene 105' was first asexually propagated by field grafting dormant hardwood scions to rootstock in 2010 in Irymple, Victoria, Australia. Fruit from the resulting sixteen grafted 'Sheegene 105' vines was first harvested in 2012. All characteristics and distinctions remain true to form and are established and transmitted through succeeding propagations.

SUMMARY OF THE INVENTION

The following are the most outstanding and distinguishing characteristics of 'Sheegene 105'. 'Sheegene 105' produces medium and naturally loose bunches. The berries produced by 'Sheegene 105' are black (5RP 3/2) and exhibit a narrow ellipsoid shape, good evenness, and crunchy, neutral flavour.

'Sheegene 105' can be distinguished from its male parent, 'Stanley Seedless' based on upon berry color, shape and length. 'Sheegene 105' produces black-colored grapes; whereas, 'Stanley Seedless' produces green yellow berries. Additionally, 'Sheegene 105' berries exhibit a narrow ellipsoid shape; whereas, 'Stanley Seedless' berries exhibit a roundish shape. The length of 'Sheegene 105' berries (21 mm on average) is also shorter than that of 'Stanley Seedless' berries (23 mm on average).

'Sheegene 105' is believed to be most similar to 'Autumn Royal'. Nonetheless, the new cultivar can be distinguished from its female parent, 'Autumn Royal', based at least upon vigor, berry shape and attachment, rudimentary seeds per berry, bunch size, and harvest period. 'Sheegene 105' displays a medium to high vigor; whereas, 'Autumn Royal' displays medium to low vigor. 'Sheegene 105' berries exhibit a narrow ellipsoid shape; whereas, 'Autumn Royal' berries exhibit an ovoid to ellipsoidal shape. The berries of 'Sheegene 105' are more strongly attached than those of 'Autumn Royal'. The berries of 'Autumn Royal' also exhibit 2-4 detectable rudimentary (aborted) seeds that each weigh about 7.2 mg. In contrast, any rudimentary seeds within the berries of 'Sheegene 105' are undetectable. Additionally, the bunches produced by 'Sheegene 105' are smaller than those of 'Autumn Royal'. 'Sheegene 105' is harvested in July in Murcia (Spain), which is earlier than the late August to early September harvest period of 'Autumn Royal' in Murcia (Spain).

'Sheegene 105' possesses some similarities with 'Summer Royal' (European PBR Certificate No. 30887). However, 'Sheegene 105' berries exhibit a narrow ellipsoid shape, whereas 'Summer Royal' berries exhibit a circular shape. The berries produced by 'Sheegene 105' are also heavier (6.6 g) than the berries produced by 'Summer Royal' (5 g).

BRIEF DESCRIPTION OF THE DRAWING

FIG. 1—Shows the form, foliage, and fruit of a 4-year-old 'Sheegene 105' vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'Sheegene 105'. The detailed description was obtained between March and November using 4-year-old plants grown in the field in Murcia, Spain. The color references are to the *Munsell Color Charts for Plant Tissue,* 1977 Edition by Munsell Color.

Classification:
- *Family.*—Vitaceae.
- *Botanical.*—*Vitis vinifera.*
- *Common name.*—Grapevine.
- *Cultivar name.*—'Sheegene 105'.

Plant:
- *Plant habit and growth.*—Semi-erect.
- *Age at maturity.*—4 years old.
- *Size* (*at maturity*).—Height: 225 cm. Width: 300 cm.
- *Vigor.*—Medium to high.
- *Productivity.*—Medium to high, 30,000-35,000 pounds/acre.
- *Rootstock.*—Name of rootstock: 1103 Paulsen Rootstock (unpatented). Age of rootstock at time of grafting: one year old.

Trunk:
- *Size.*—Diameter: 8.125 cm.
- *Surface texture.*—Very smooth, the outer layer easily removed.
- *Bark color.*—Exterior: 5 YR 3/2. Interior: 5 YR 3/4.

Canes:
- *Size.*—Diameter: 9 mm. Length: 180 cm.
- *Surface texture.*—Mature cane: smooth. Immature cane: smooth, very finely ribbed.
- *Form* (*woody shoot cross section form*).—Pith in center with diaphragm at nodes.
- *Color.*—Mature: 2.5 GY 5/6 at 5 months (anthocyanins: 2.5 YR 4/6). Immature: 5 GY 5/6 at 4 weeks.
- *Internode length* (*upper mature sun cane*).—13.5 cm (on June 15).

Time of bud burst: February 27.

Tendrils:
- *Form.*—Mostly trifid.
- *Size.*—Medium.
- *Length.*—23 cm.
- *Diameter.*—2.25 mm.
- *Texture and distribution of tendril at each node beginning at base.*—Smooth, discontinuous, 0000001010001010101 (0 means no tendril at that node and 1 means there is tendril at the node).
- *Color.*—Mature: 2.5 GY 7/6 at 4 weeks. Immature: 2.5 GY 6/6 at 10 days. Anthocynanin: Mature: 7.5 YR 5/4. Immature: 7.5 YR 4/4.

Growing tips (young shoot):
- *Pubescence.*—Present.
- *Color.*—5 GY 5/6.
- *Anthocynanin.*—Absent.
- *Shape.*—Fully open.
- *Apex.*—Triangular.

Leaves:
- *Shape.*—Cuneiform.
- *Apex.*—Pointed.
- *Base.*—Rounded.
- *Number of lobes.*—5.
- *Depth of upper lateral sinuses of mature leaves.*—Medium.
- *Arrangement of lobes of upper lateral sinuses on mature leaves.*—Slightly overlapped.
- *Margin.*—Irregular teeth. Length of teeth on margin: 2-10 mm. Shape of teeth on margin: mostly straight, very few convex. Texture (mature leaf): Upper surface: smooth, flat. Lower surface: glabrous, smooth. Size: Immature: Length: 9.5 cm at 10 days. Width: 10 cm at 10 days. Mature: Length: 19 cm at 4 weeks. Width: 18 cm at 4 weeks. Color: Immature leaf: Upper surface: 5 GY 4/6. Lower surface: 5 GY 5/4. Color: Mature leaf: Upper surface: 5 GY 4/4. Lower surface: 5 GY 5/4. Venation: Pattern: primary veins on upper leaf are flat, veins on lower leaf are raised. Color: Upper surface: 2.5 GY 6/6. Lower surface: 2.5 GY 7/6. Petiolar sinus: half open, brace-shaped. Petiole: Length: 8.5 cm. Diameter: 2.85 mm. Color: 2.5 GY 6/6 (anthocyanins: 10 R 5/6).

Floral cluster:
- *General description and location.*—Mostly 6th or 7th node, 100% with shoulders.
- *Quantity of inflorescences per cluster.*—900.
- *Size.*—Length: 20 cm. Width: 13.9 cm (spread); 9.5 cm (hanging).
- *Peduncle.*—Length: 4 cm.
- *Inflorescences.*—Hermaphroditic.
- *Stamens.*—Straight, 2.6 mm.
- *Anthers.*—Small and nondescript.
- *Date of bloom.*—Start April 23; 50% April 27; 100% May 6.
- *Pollen amount.*—Abundant.
- *Calyptra.*—5 segments with complete separation.
- *Calyptra color.*—2.5 GY 5/8.

Fruit:
- *Time of year of commercial harvest and shipment.*—Early season, mid of July.
- *Keeping quality.*—After 30 days, the variety shows slight symptoms of dehydration of the pedicel and secondary stem, and berry shatter. Excellent eating quality, the berries keep the neutral flavor and crunchy texture.
- *Cluster* (*primary bunches*).—General size: medium 665 g tipped; 870 g not tipped. Length (without peduncle): 23 cm tipped; 30 cm not tipped. Width: 16 cm (hanging), 28.6 cm (shoulders spread). Density: loose. Peduncle: Length: 6.3 cm. Diameter: 6.6 cm. Color: 2.5 GY 5/6, anthocyanins: 5 R 3/6.
- *Number of berries per cluster.*—142 tipped; 160 not tipped.
- *Berry.*—Size: medium (6.6 g). Diameter: 18.7 mm. Length: 28.5 mm. Shape: narrow ellipsoid. Uniformity: uniform. Brix content: 18° Brix. Skin color without bloom: 5 RP 3/2. Skin color with bloom: 5 RP 3/2. Pedicel: Length: 9.3 mm. Diameter: 1.3 mm. Color: 5 GY 6/6. Strength of attachment to berry: strong.

*Cluster* (*secondary bunches*).—General size: medium/large, 260 g. Length (without peduncle): 15 cm. Width: 100 mm (hanging), 174 mm (shoulders spread). Density: loose. Peduncle: Length: 6.5 cm. Diameter: 4.3 mm. Color: 2.5 GY 5/6.

*Number of berries per cluster.*—61.

*Berry*.—Size: small, 4 g. Diameter: 19 mm. Length: 25 mm. Shape: narrow ellipsoid. Uniformity: uniform. Brix content: 17.9° Brix. Skin color: 5 RP 3/2. Pedicel: Length: 9.2 mm. Diameter: 1.2 mm. Color: 5 GY 6/6. Strength of attachment to berry: strong.

Berry flesh:

*Color.*—2.5 GY 7/4.

*Juice color*.—Clear, 5Y 8/4.

*Juice production*.—Very high (58%).

*Thickness of skin*.—Medium.

*Flavor*.—Neutral.

*Fragrance*.—Neutral.

*Texture*.—Very crisp (56 shores).

*Seeds*.—Seed rudiments not detectable.

*Use*.—Table.

Disease and insect resistance: This cultivar is susceptible to the main diseases of its species, such as *Erysiphe necator, Plasmopara viticola, Botrytis cinerea, Daktulosphaira vifoliae, Ceratitis capitata, Planococcus ficus, Planococcus citri*, and *Empoasca vitis*.

What is claimed is:

1. A new and distinct variety of grapevine called 'Sheegene 105' as shown and described herein.

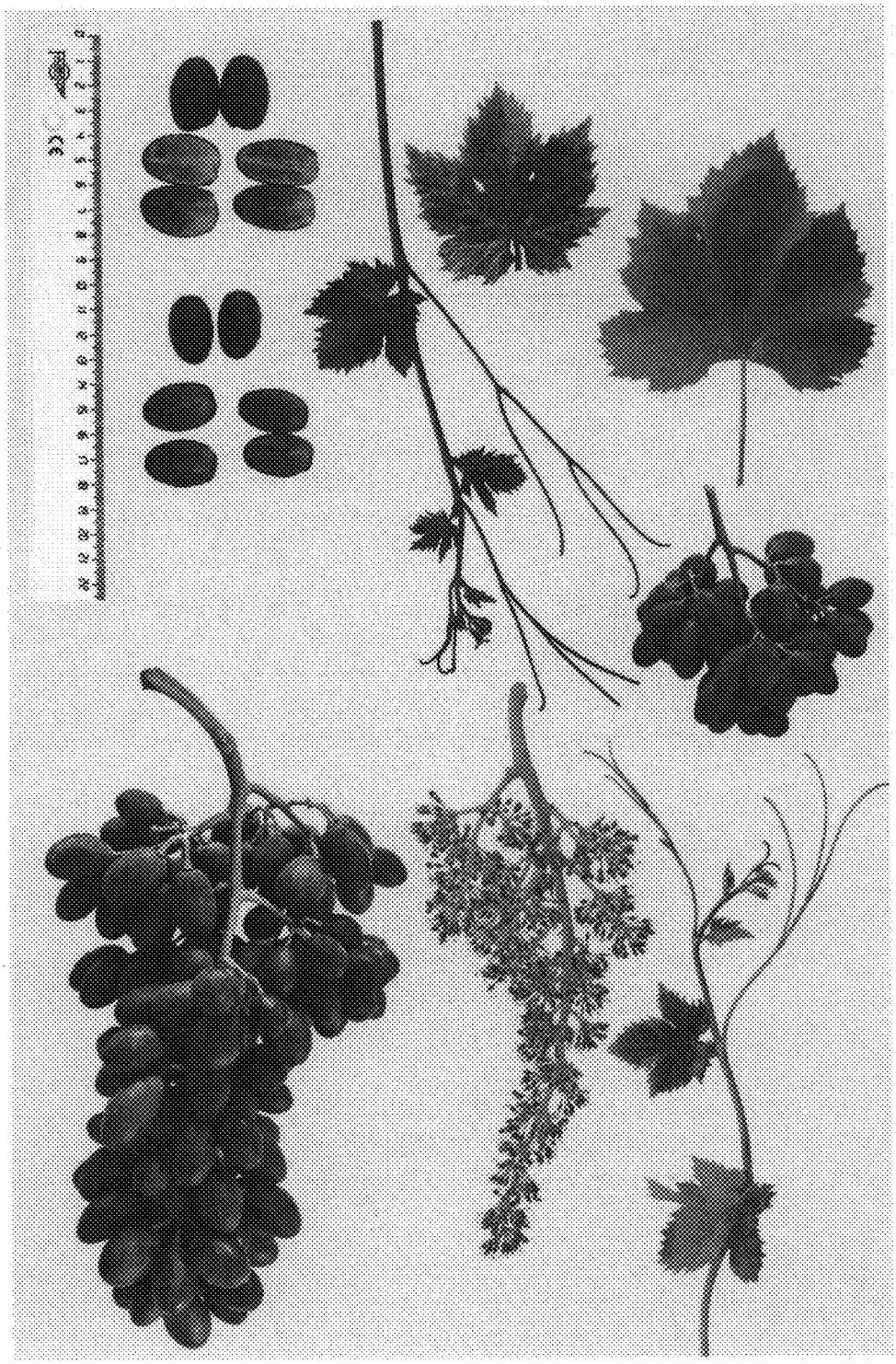

* * * * *